United States Patent [19]
Adams et al.

[11] Patent Number: 5,318,533
[45] Date of Patent: Jun. 7, 1994

[54] BALLOON CATHETER INFLATION DEVICE INCLUDING APPARATUS FOR MONITORING AND WIRELESS TRANSMISSION OF INFLATION DATA, AND SYSTEM

[75] Inventors: Daniel O. Adams, Orono; David J. Haskvitz, Golden Valley; Thomas J. Holman, Minneapolis; William H. Penny, St. Anthony; David J. Serdar, Shorewood; John M. Yates, Plymouth, all of Minn.

[73] Assignee: SciMed Life Systems, Inc., Maple Grove, Minn.

[21] Appl. No.: 839,628

[22] Filed: Feb. 21, 1992

[51] Int. Cl.$^5$ ..................... A61M 29/00; A61M 5/00
[52] U.S. Cl. ..................... 604/97; 604/100; 604/110; 128/903
[58] Field of Search ............... 128/903; 604/96-103, 604/110; 606/192-196; 340/870.18

[56] References Cited

U.S. PATENT DOCUMENTS

| | | | |
|---|---|---|---|
| D. 309,663 | 7/1990 | Robinson | D24/54 |
| 3,082,414 | 3/1963 | Papaminas | 340/279 |
| 3,350,944 | 11/1967 | DeMichele | 73/398 |
| 4,089,329 | 5/1978 | Couvillion, Jr. et al. | 128/2 |
| 4,248,241 | 2/1981 | Tacchi | 128/671 |
| 4,332,254 | 6/1982 | Lundquist | 128/344 |
| 4,356,486 | 10/1982 | Mount | 340/870.38 |
| 4,439,186 | 3/1984 | Kuhl | 604/99 |
| 4,471,786 | 9/1984 | Inagaki et al. | 128/748 |
| 4,519,401 | 5/1985 | Ko et al. | 128/748 |
| 4,522,213 | 6/1985 | Wallroth et al. | 128/716 |
| 4,610,256 | 9/1986 | Wallace | 128/675 |
| 4,633,304 | 12/1986 | Nagasaki | 358/93 |
| 4,697,574 | 10/1987 | Karcher et al. | 604/99 |
| 4,781,192 | 11/1988 | Demer | 604/99 |
| 4,796,641 | 1/1989 | Mills et al. | 128/748 |
| 4,846,153 | 7/1989 | Berci | 604/99 |
| 4,846,191 | 7/1989 | Brockway et al. | 128/748 |
| 4,865,587 | 9/1989 | Walling | 604/99 |
| 4,872,483 | 10/1989 | Shah | 604/99 |
| 4,958,645 | 9/1990 | Cadell et al. | 128/903 |
| 4,981,141 | 1/1991 | Segalowitz | 128/696 |
| 5,004,472 | 4/1991 | Wallace | 606/194 |
| 5,007,919 | 4/1991 | Silva et al. | 604/99 |
| 5,009,662 | 4/1991 | Wallace et al. | 606/192 |
| 5,019,041 | 5/1991 | Robinson et al. | 604/97 |
| 5,021,046 | 4/1991 | Wallace | 604/97 |
| 5,048,060 | 1/1992 | Freund et al. | 606/192 |
| 5,057,078 | 10/1991 | Foote et al. | 604/99 |
| 5,135,488 | 8/1992 | Foote et al. | 604/99 |
| 5,152,776 | 10/1992 | Pinchuk | 606/192 |
| 5,168,757 | 12/1992 | Rabenau et al. | 604/99 |
| 5,171,299 | 12/1992 | Heitzmann et al. | 604/100 |
| 5,201,753 | 4/1993 | Lampropoulos et al. | 606/192 |
| 5,209,732 | 5/1993 | Lampropoulos et al. | 604/99 |
| 5,215,523 | 6/1993 | Williams et al. | 604/97 |

FOREIGN PATENT DOCUMENTS

WO90/11104 10/1990 PCT Int'l Appl. ............ A61B A2

OTHER PUBLICATIONS

Merit Medical Inflator Inflation System Instruction Manual, Merit Medical Systems, Inc., Salt Lake City, Utah (1989).

Primary Examiner—C. Fred Rosenbaum
Assistant Examiner—Mark Bockelman
Attorney, Agent, or Firm—Kinney & Lange

[57] ABSTRACT

An inflation device includes a syringe forming a cylindrical chamber containing a plunger carrying a stopper or piston arrangement. The chamber is designed to contain an inflation fluid and is in fluid communication with the lumen of a balloon catheter. Movement of the plunger within the chamber will increase or decrease the pressure of the fluid within the chamber and lumen, thereby inflating or deflating the balloon at the distal end of the catheter. A pressure sensor is mounted to the housing in fluid communication with the lumen and is electrically connected to a battery-operated transmitter. The transmitter broadcasts signals representing pressure within the lumen and balloon to a remote receiver. The receiver includes a microprocessor containing a clock and operable to display time and pressure data. A flexible insulator strip is interposed between the battery and the transmitter circuit to prevent operation of the transmitter until desired by the cardiologist. The housing of the inflation device may be opened to remove the batteries for separate disposal and to render the circuit inoperative to prevent reuse. A look-up table associated with the microprocessor permits display of balloon diameter during the procedure.

31 Claims, 5 Drawing Sheets 5,318,533

BALLOON CATHETER INFLATION DEVICE INCLUDING APPARATUS FOR MONITORING AND WIRELESS TRANSMISSION OF INFLATION DATA, AND SYSTEM

BACKGROUND OF THE INVENTION

This invention relates to percutaneous transluminal coronary angioplasty (PTCA), and more particularly, to an inflation device for inflating a balloon of a PTCA catheter, the inflation device having means for monitoring inflation data and transmitting such data to a receiver and display device. The invention also relates to a monitor and communication system by which inflation data of an inflation device are monitored and transmitted to a remote receiver for recording and display of information concerning those data.

Coronary angioplasty is an accepted medical procedure for dilatating a stenosis which partially blocks an artery. The procedure is carried out by advancing a balloon carried by a dilatation catheter until the balloon is across the stenosis. The balloon is inflated, usually to a pressure of several atmospheres, to dilatate the stenosis and open the artery. The balloon is then deflated and retracted from the arterial system. Typically, the balloon is constructed of a high-strength polymeric material which assumes a prescribed diameter when inflated by a prescribed pressure. Hence, the dilatation process is carefully controlled by the balloon selected for the procedure as well as the pressure applied to the balloon.

It is necessary, during the procedure, that the balloon be advanced and retracted in the arterial system. This is accomplished by advancing the balloon in a deflated state, inflating it when it is positioned across the stenosis, and thereafter deflating the balloon to retract it from the arterial system. Thus, the balloon is inflated in situ when it is positioned across the stenosis.

In order to assure proper inflation of the dilatation balloon, it is important that the cardiologist knows the inflation pressure applied to the balloon. The balloon, when inflated, effectively blocks the artery. Therefore, it is also important that the duration of the inflation is known to the cardiologist. Since the angioplasty procedure ordinarily requires several inflations of the balloon at the location of the stenosis, it is also desirable that the cardiologist know the number of inflations which have been conducted.

Heretofore, inflation devices included pressure gauges attached to the inflation device in fluid communication with the lumen of the balloon catheter. The pressure gauge on the inflation device displayed the pressure within the lumen, and hence, within the dilatation balloon, the pressure usually being displayed in atmospheric pressure. Examples of balloon inflation devices having pressure gauges may be found in U.S. Pat. No. 5,019,041 granted May 28, 1991 to Robinson et al. and U.S. Pat. No. D-309,663 granted Jul. 31, 1990 to Robinson. Using such inflation devices, the cardiologist would determine the pressure of the inflation by observing the pressure gauge, would determine the duration of inflations by observing elapsed time on the cardiologist's watch or on a clock in the operating room, and would observe the number of inflations by mentally keeping track of them.

The memory of the persons present during the procedure, as well as any procedural logs maintained by them, served as the only record of the pressures, durations, and numbers of inflations performed during the angioplasty procedure. Memories, and human recorded logs, were not always accurate. Thus, even during the procedure, the cardiologist could lose track of the number of inflations, the duration of any particular inflation, or even be distracted from observing the pressure gauge during the inflation procedure.

The inflation device was often awkward to operate, particularly due to the positioning of the pressure gauge on the inflation device housing. Since the cardiologist is also concerned with operating other equipment during the procedure, such as positioning the guide catheter, balloon catheter and/or any guidewire, manipulating the inflation device housing so that the pressure gauge could be observed was an added annoyance to the cardiologist.

As a result of some of these concerns, attempts have been made to electronically monitor the inflation pressures through the use of a sensor mounted to the inflation device, with a separate display device for displaying the inflation pressure and duration. Examples of these devices are found in Wallace U.S. Pat. Nos. 5,004,472 and 5,021,046, Wallace et al U.S. Pat. No. 5,009,662 and Foote et al. PCT Publication No. WO 90/11040. However, these prior devices physically connected the display device to the inflation device by electronic cables which interfere with the manipulation of the inflation device, so the awkwardness of manipulating the inflation device was not completely alleviated.

The inflation device should be sterile. Under most circumstances, the inflation device is manufactured and supplied to the cardiologist in a sterile condition and is simply discarded after each procedure. However, the electronic cable connections between the electronic sensor and the monitor device are costly, representing a significant replacement expense if the cables are also discarded. While the cables and sensor devices could be sterilized, that approach is also quite costly. A less desirable alternative is simply not to replace or sterilize the cables, but that alternative is not acceptable to most cardiologists.

SUMMARY OF THE INVENTION

An inflation device according to the present invention includes a syringe forming a cylindrical chamber containing a plunger carrying a stopper or piston arrangement. The chamber is designed to contain an inflation fluid and is in fluid communication with the lumen of a balloon catheter. Movement of the plunger within the chamber will increase or decrease the pressure of the fluid within the chamber and lumen, thereby inflating or deflating the balloon at the distal end of the catheter. A pressure sensor is mounted to the housing in fluid communication with the lumen and is electrically connected to a battery-operated transmitter. The transmitter transmits signals representing pressure within the lumen and balloon to a remote receiver and display unit. The receiver and display unit includes a microprocessor containing a clock and operable to display time and pressure data.

One feature of the invention resides in the provision of a flexible insulator strip interposed between the battery and the transmitter circuit to prevent operation of the transmitter until desired by the cardiologist.

Another feature of the present invention resides in the construction of the housing of the inflation device to permit removal of the batteries for separate disposal, the opening of the housing rendering the circuit inoperative.

Another feature of the present invention resides in the provision of a look-up table associated with the microprocessor, the look-up table containing relational data relating balloon diameter to pressure, the microprocessor being responsive to the pressure data and to data identifying the dilatation balloon to operate the display unit to display balloon diameter.

DETAILED DESCRIPTION OF THE PREFERRED EMBODIMENTS

Figure 1:
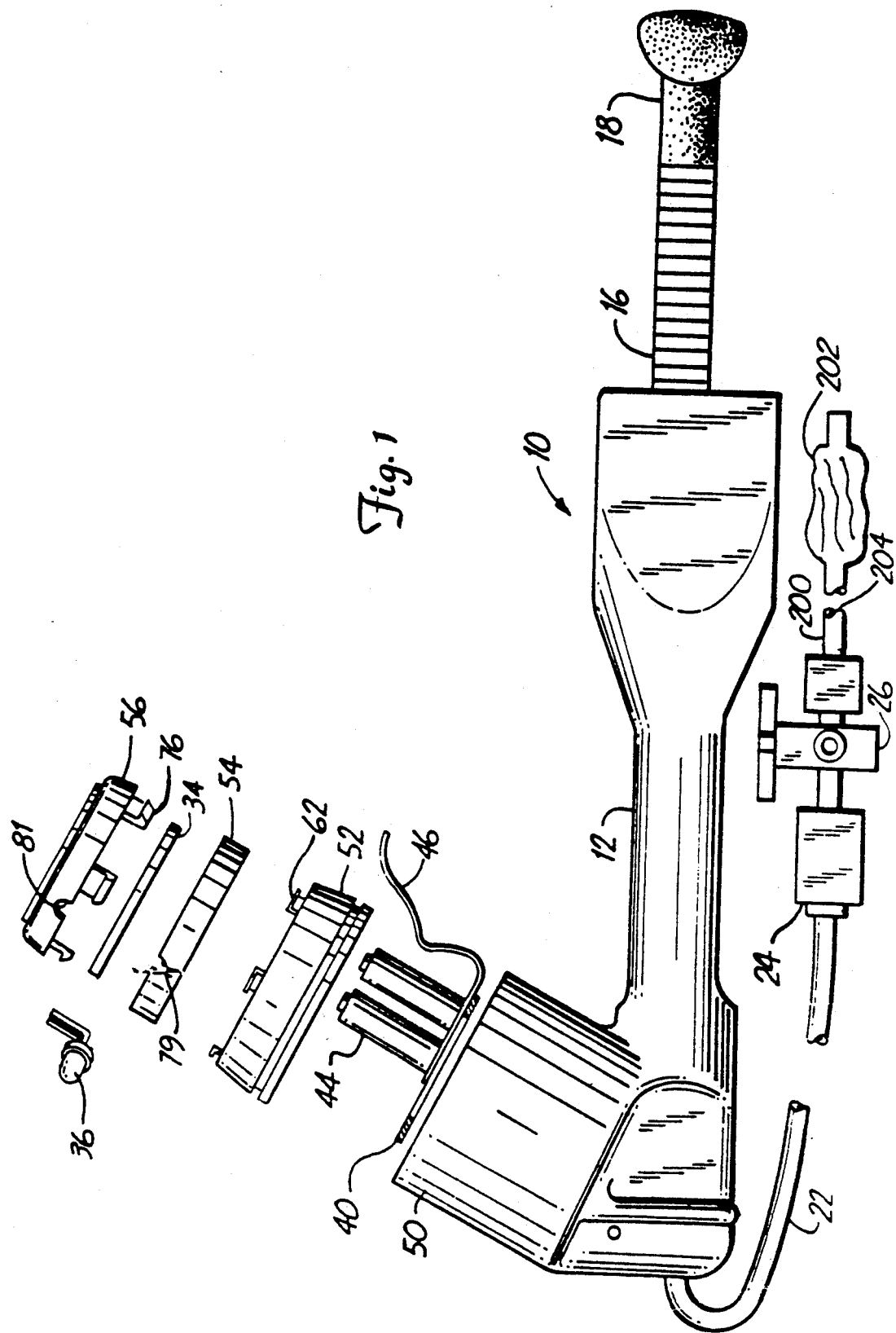
FIG. 1 is a partly exploded side view of an inflation device in accordance with the presently preferred embodiment of the present invention.

FIG. 1 is a partly exploded side view of inflation device 10 in accordance with the presently preferred embodiment of the present invention. Inflation device 10 includes a housing 12 forming a syringe comprising cylindrical chamber 14 (FIG. 2) containing a pressure fluid. Threaded plunger 16 is threadably attached to housing 12 and includes a stopper or piston (not shown) attached to the distal end thereof and handle 18 attached to the proximal end. Rotation of handle 12 causes reaction of the threaded portions of the plunger and housing to thereby move plunger 16 and its stopper or piston along the axis of chamber 14 to thereby selectively increase or decrease the fluid pressure within chamber 14. Alternatively, a mechanical latch (not shown) may disengage the threads for rapid movement of the plunger relative to the housing, as more fully described in the aforementioned Robinson et al patent. Chamber 14 is in fluid communication with the lumen 20 (FIG. 2) of flexible tube 22, whose distal end terminates in luer fitting 24. A stopcock or valve 26 is connected to fitting 24 for connection to the proximal end of balloon catheter 200 having dilatation balloon 202 connected in fluid communication to lumen 204 at the distal end of the catheter. Lumen 20 of tube 22 is thus in fluid communication with lumen 204 of balloon catheter 200.

Figure 2:
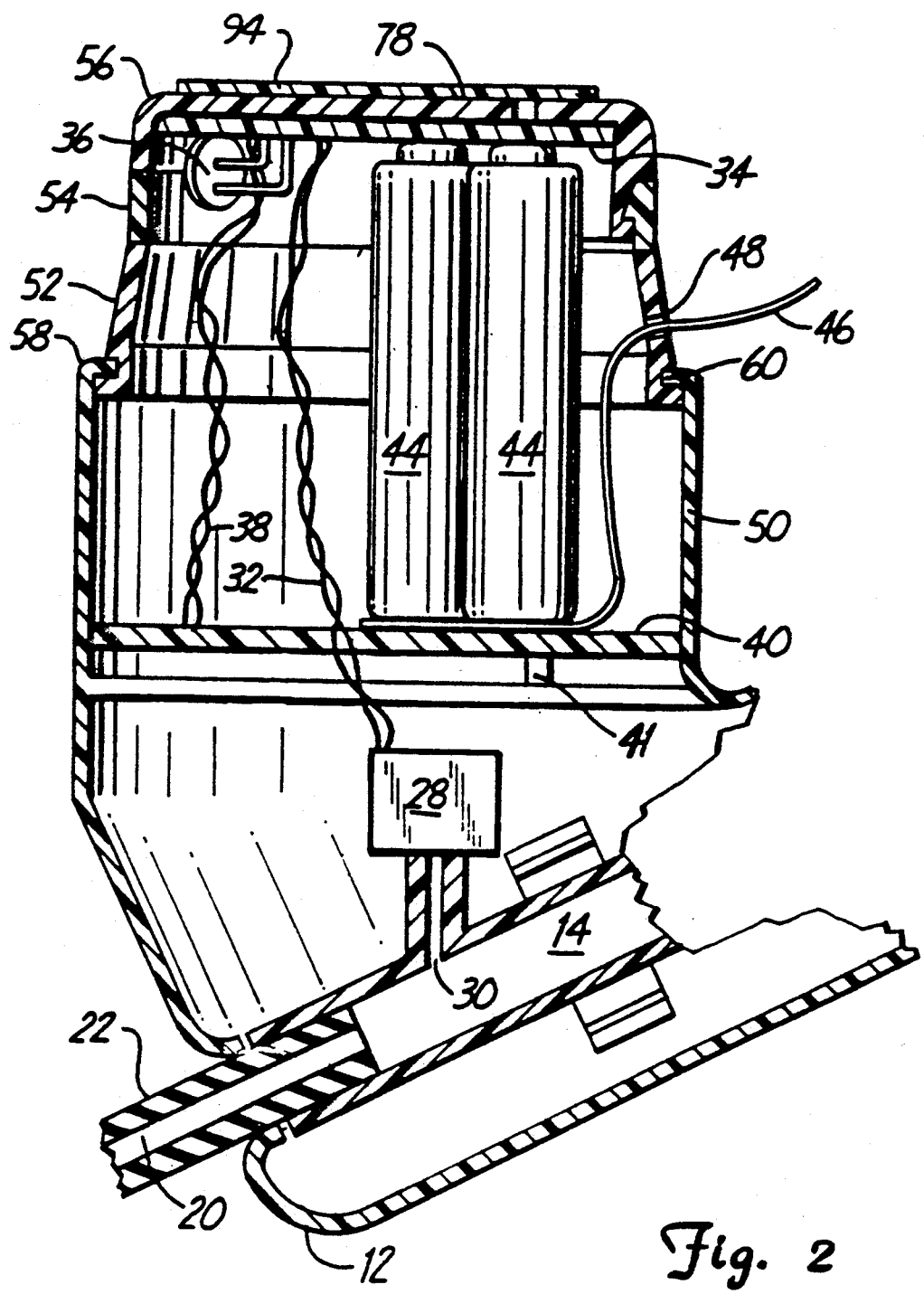
FIG. 2 is a section view of a portion of the inflation device illustrated in FIG. 1.

As shown in FIG. 2, pressure sensor 28 is in fluid communication through port 30 to chamber 14 of the syringe. Pressure sensor 28 is an electronic pressure sensor adapted to provide an electronic signal representative of the pressure within chamber 14, examples of two suitable pressure sensors being one available from Lucas Nova Sensor of Fremont, Calif. and another available from IC Sensors of Milpitas, Calif. Each of these sensors produces an electronic signal having a voltage level representative of pressure. Sensor 28 is electrically connected through frangible fine-gauge wires 32 to circuit board 34. Light-emitting diodes 36 and 37 (FIG. 4) are mechanically and electrically mounted to board 34, which in turn is connected by frangible fine-gauge wires 38 to circuit board 40 supported by shoulders 41 of housing 12. Wires 32 and 38 are of a fine gauge, such as 26 to 28 gauge, or are thin foil strips, arranged to easily break or sever upon application of small mechanical loads. Batteries 44 are sandwiched between circuit board 40 and circuit board 34 with flexible insulating strip 46 being sandwiched between one terminal of batteries 44 and one of the circuit boards, such as circuit board 40, to electrically insulate the batteries from the circuit. Strip 46 extends through slot 48 in the housing assembly so that the strip may be withdrawn to energize the circuits on boards 34 and 40 when inflation device 10 is to be used.

Optionally, membrane switch 94 is attached to the top surface 78 of member 56 and is attached to a latch circuit 96 (FIG. 4) to initiate operation of the apparatus. Membrane switch 94 and latch 96 may be included in addition to, or in place of, flexible strip 46.

It is important that PTCA catheters, and inflation devices for inflating the balloons of such catheters, be sterile. Such devices are manufactured under sterile conditions and supplied to the cardiologist in sterile packages. They are intended to be used once, and then discarded. It is, therefore, desirable to discourage reuse of catheters and inflation devices, such as by rendering them inoperative after a single use. In the case of the inflation device according to the present invention, the batteries operating the transmitter on circuit boards 34 and 40 are electrically connected to the circuit boards by removing flexible strip 46. Once the flexible strip is removed, it cannot be easily reinserted through slot 48 and between the batteries and the circuit board to preserve the batteries for later reuse. Also, as will become evident herein, it is preferred that the housing cannot be easily opened to reinsert the flexible strip without disabling the circuit. Thus, once energized, the inflation device according to the present invention will perform its function, whereupon the inflation device is discarded.

Environmental concerns make it desirable to separately dispose of batteries 44 and/or the battery assembly. The preferred batteries 44 are low mercury content alkaline, manganese dioxide ($Zn/MnO_2$) batteries. Consequently, one feature of the invention is the provision of a housing assembly to permit removal of the batteries or battery assembly, while rendering the inflation device inoperative for future use. More particularly, the housing assembly includes a three-piece assembly comprising housing members 52, 54 and 56 which form an enclosure to house the batteries and electronics of the present invention to permit easy disassembly of the housing to enable removal of the batteries and at the same time rendering the electronics inoperative. Members 52, 54 and 56, which are preferably constructed of a rigid plastic, such as polycarbonate or the like, are shown in detail in FIG. 3.

Member 52 includes slot 58 arranged to receive lip 60 of cylindrical portion 50 of housing 12 to thereby fasten the member to cylindrical portion 50. Member 52 includes a plurality of C-shaped clamp fasteners 62 integrally formed at the upper portion thereof internally within enclosure formed by the member. Clamp fasteners 62 include circumferentially-disposed internal surfaces 66 at the upper portion of clamp fasteners 62 arranged to engage respective surfaces 68 of fasteners 64 on member 54. Fasteners 64 are integral to member 54 and internal to the enclosure formed by the member and include a forward sloped circumferentially-disposed ramp surface 70 at the forward portion thereof. Circumferentially-disposed surfaces 68 are, slightly recessed from ramp surfaces 70 to form a small radial lip therebetween. Members 52 and 54 are fastened together by positioning the members relative to each other with their circular edges confronting. The members are rotated with respect to each other so that surfaces 66 of clamp fasteners 62 engage ramp surfaces 70 of fasteners 64 and are cammed by the ramp surfaces until received by the recessed surfaces 68. Fasteners 62 and 64 are thereby fastened together to fasten members 52 and 54 together, locking them into a releasably fastened engagement.

Member 54 also includes internal recesses 72 arranged to receive lips 74 of snap latches 76 on member 56. Recesses 72 and latches 76 are also internal to the enclosure formed by their respective members 54 and 56. Semi-circular cutouts 79 and 81 are provided in members 54 and 56 to receive light-emitting diodes 36 and 37. Guides 55 are provided to align members 54 and 56 during assembly.

The apparatus is assembled by rigidly fastening member 52 to cylindrical portion 50 (such as by thermal forming), and thereafter assembling member 54 to member 52 as described. The electronics of boards 40 and 34 and batteries 44, including insulator strip 46, are positioned within the enclosure formed by members 50, 52 and 54, and light-emitting diodes 36 and 37 are positioned in recesses 79 in member 54. Preferably, there are at least two light-emitting diodes 36 and 37 nested in respective openings 79 about the periphery of member 54. The free end of strip 46 is inserted through slot 48 of member 52. Member 56 is thereupon aligned with light-emitting diodes 36 and 37 and snapped in place so that latches 76 engage recesses 72.

After the inflation device has served its purpose and it is desired to dispose of the device, the housing may be destructively disassembled by relatively rotating members 52 and 54. More particularly, upon rotation, surfaces 66 of the clamp fasteners will cam against the lip formed by ramp surface 70 and recessed surface 68 of fasteners 64 to permit disassembly of the unit. Thus, the enclosure formed by members 50, 52, 54 and 56 may be opened to remove the battery assembly or batteries 44 for separate disposal. However, since light-emitting diodes 36 and 37 are rigidly secured in the aperture formed by slots 79 and 81 in members 54 and 56, the light-emitting diodes secure the position of circuit board 34 in the top portion of the housing. Hence, the opening the housing between members 52 and 54 will cause circuit board 34 to become separated from transducer 28, thereby breaking fine-gauge wires 32 connecting board 34 to transducer 28 to disable the electronic circuit on boards 34 and 40. Likewise, if the separation of the housing is performed at an ordinary pace (without extreme care), the fine-gauge wires 38 between circuit boards 34 and 40 will also break, thereby further disabling the electronic circuit. Hence, the electronic circuit is rendered inoperative and can not be easily reconstructed.

Figure 4:
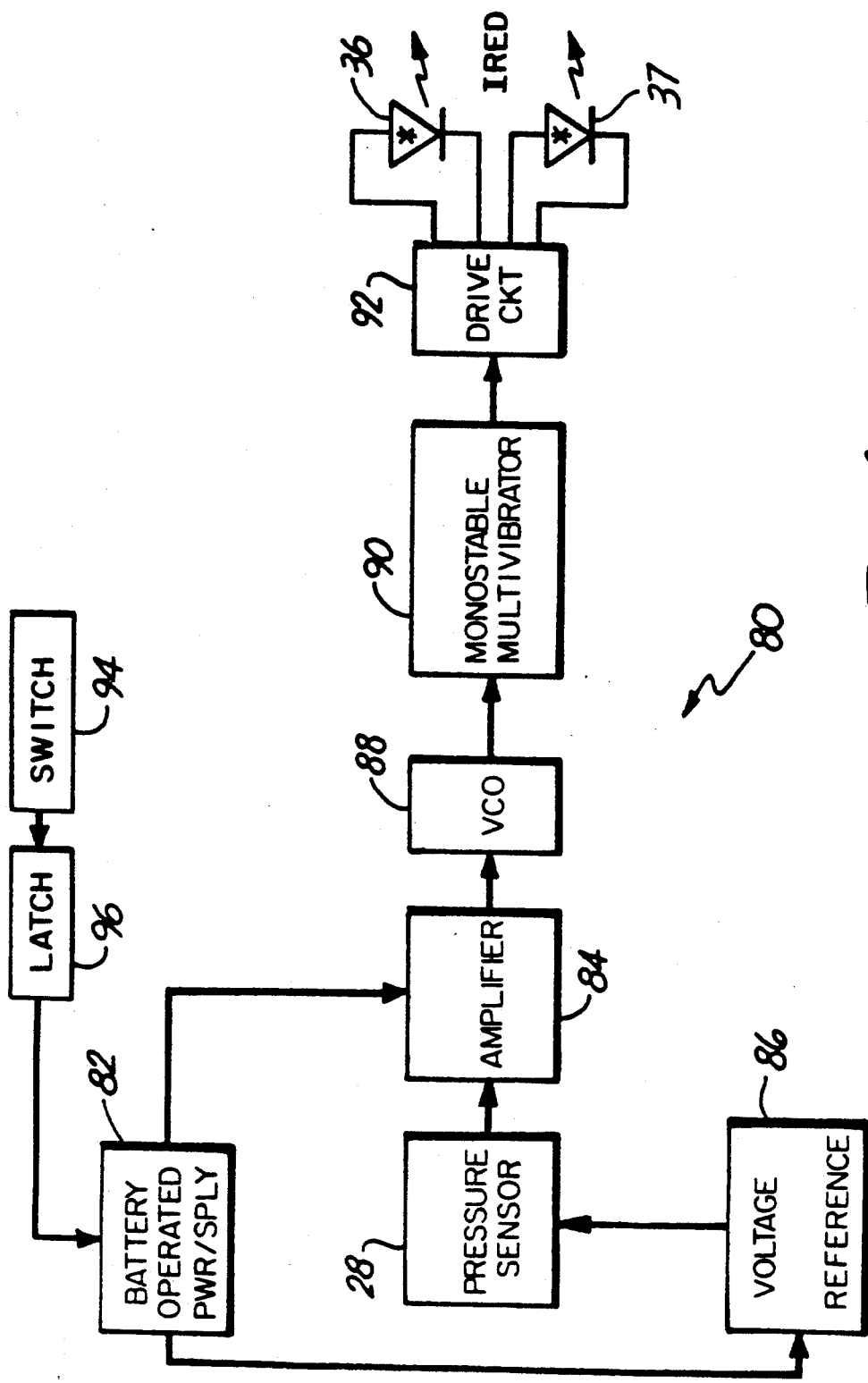
FIG. 4 is a block diagram of a transmitter circuit in accordance with the presently preferred embodiment of the present invention.

FIG. 4 illustrates infrared transmitter 80 contained in housing 12, and particularly on circuit boards 34 and 40 (FIGS. 1 and 2). Transmitter 80 includes a battery-operated power supply 82, powered by batteries 44 (FIGS. 1 and 2) to provide low voltage power (3.0 V) to DC amplifier 84 and voltage reference source 86. Power supply 82 is initiated by removal of flexible strip 46 (FIG. 2), as previously described, and/or by operation of membrane switch 94 attached to the top of housing member 56, as previously described. If membrane switch 94 is provided, latch 96 (which may be incorporated onto circuit board 34) is responsive to operation of membrane switch 94 to permanently operate the circuit of FIG. 4.

Source 86 provides a reference voltage to pressure sensor 28, which in turn provides an electrical signal input to amplifier 84. Pressure sensor 28 is a piezo-resistive bridge-type pressure sensor which provides an electronic signal output proportional to the pressure in chamber 14. The signal from pressure sensor 28 is amplified by amplifier 84 to drive voltage-controlled oscillator (VCO) 88 thereby deriving a signal having a frequency representative of the voltage amplitude of the signal from pressure sensor 28, and hence of the pressure in chamber 14. VCO 88 is designed to vary between about 5 and 15 kilohertz (KHz) over the operating range of pressure sensor 28. More particularly, since pressure sensor 28 operates to a range up to about 20 to 25 atmospheres, VCO 88 is designed to provide a signal varying between 5 and 15 KHz as the pressure sensed by sensor 28 varies between about 0 and 25 atmospheres. VCO 88 provides an input to monostable (single-shot) multivibrator 90 which in turn provides a short duration pulse output for each cycle of oscillation from VCO 88.

It is preferred the duty cycle of the pulse signal produced by multivibrator 90 be small compared to the duration of each cycle to thereby conserve battery power and to allow drive circuit 92 to generate a high current pulse through light-emitting diodes 36 and 37. A pulse duration of about 2 to 5 microseconds has been found to be adequate for the intended purposes. Hence, the output from multivibrator 90 is a pulse signal wherein each pulse has a duration of about 2 to 5 microseconds and the pulse signal varies in repetition rate by about 10 KHz, between 5 and 15 KHz, depending on the pressure sensed. Drive circuit 92 is responsive to the pulses from multivibrator 90 to drive light-emitting diodes 36 and 37 which transmit pulses in the infrared region (wavelength between about 880 to 940 nm), the pulses having a low duration (2 to 5 microseconds), a high current (about one ampere) and being at a repetition rate between 5 and 15 KHz, depending on the pressure sensed by sensor 28. Thus, transmitter 80 serves to broadcast a wireless transmission of data signals representing the pressure within chamber 14, and hence within lumen 204 and balloon 202.

Figure 3:
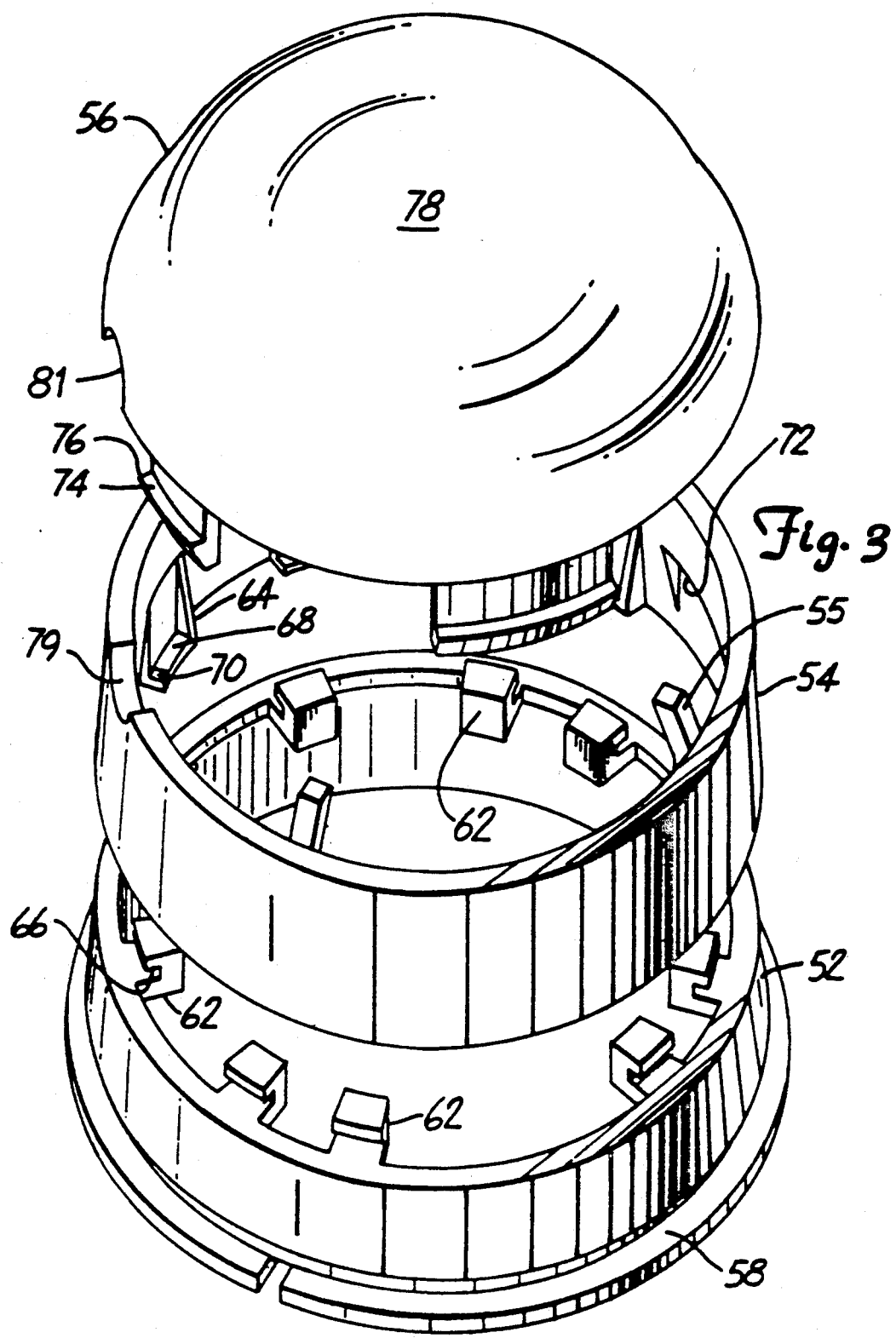
FIG. 3 is an exploded perspective view of a portion of a destructible housing for the apparatus illustrated in FIGS. 1 and 2.

Although FIGS. 1-3 illustrate a single light-emitting diode 36, it is preferred that there be at least two such diodes, arranged at approximately 90° to 120° from each other about the periphery of members 54 and 56. With such an arrangement, the transmitted signal will be transmitted over a wide physical range within the operating room, usually of the order of about 135° about the inflation device. This insures that the signal will be received by the receiver of FIG. 5, regardless of the orientation of the inflation device.

Figure 5:
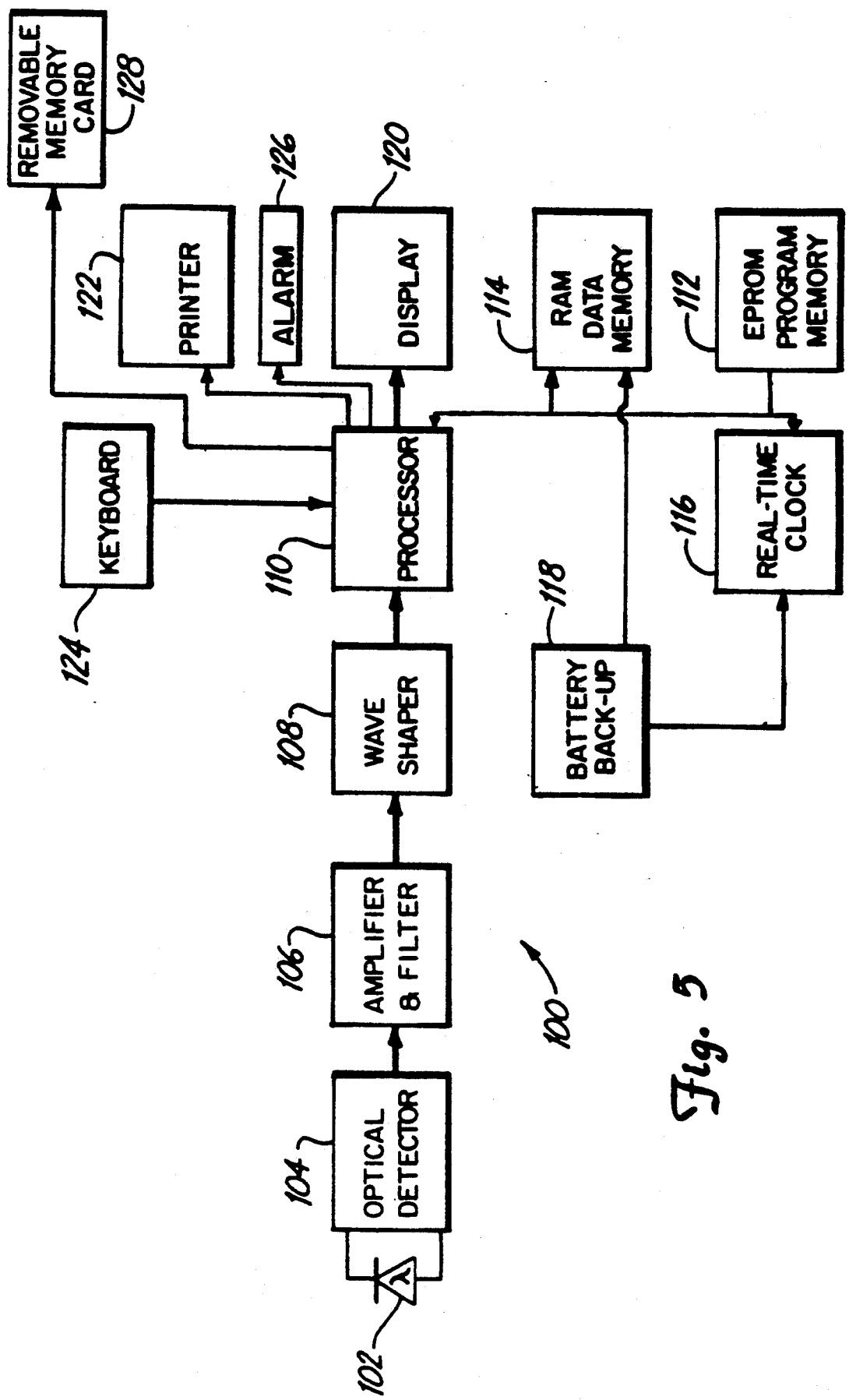
FIG. 5 is a block diagram of a receiver and processor circuit in accordance with the presently preferred embodiment of the present invention.

Receiver 100 illustrated in FIG. 5 includes one or more light sensitive diode(s) 102 which receives the wireless infrared signal broadcast or transmitted by light-emitting diodes 36 and/or 37. Diode 102 is connected to optical detector circuit 104 to generate a signal whose frequency is dependent on the pulse repetition rate of the received infrared signal from transmitter 80. The signal is amplified by amplifier 106 and shaped into square waves by wave-shaper 108 for input into microprocessor 110. Microprocessor 110 includes an EPROM program memory 112 and a RAM data memory 114. Memory 112 contains the software program for operating processor 110, whereas memory 114 stores data processed by the processor for display and/or later recording. Real time clock 116 generates time information, and battery backup 118 maintains the operation of clock 116 and the contents of memory 114 in the event of a power failure. Data is processed by microprocessor 110 for storage in memory 114 as well as for display on display device 120. Thus, RAM memory 114 contains data regarding the history of the procedure, including pressures and times of inflation. Data may be printed to a permanent record by printer 122. Keyboard 124 provides input to the microprocessor for inputting other data, such as patient information and preestablished limits to pressure and duration. Alarm 126 is responsive to microprocessor 110 to provide an audible and/or visual alarm in the event a limit is exceeded. Data memory card 128 is optionally provided to permit patient data to be pre-recorded thereon and to permit data to be recorded concerning the history of the procedure, the memory card being a permanent part of the patient's record.

Conveniently, at least display device 120, alarm 126 and light sensitive diode 102 are in the room where the angioplasty procedure is being performed. For example, these units may be enclosed in a housing mounted to the wall of the operating room or to an IV pole in the view of the cardiologist performing the procedure. It may be convenient to enclose the other components of FIG. 5 in the same housing, or they may be at a different location.

In operation of the apparatus, a balloon catheter 200 is connected to the luer device 24 or fitting 26 (FIG. 1) and advanced in the arterial system of the patient until the balloon 202 is across the stenosis. Insulator strip 46 is removed to energize the transmitter circuit, and the receiver circuit is energized through the local power system of the hospital. The cardiologist, operating plunger 16, increases the pressure within lumen 20 to thereby inflate the dilatation balloon 202 to dilatate the stenosis. Fluid pressure within the lumen reacts through port 30 on sensor 28, which operates transmitter to transmit infrared pulses, heretofore described, to light sensitive diode 102 of receiver 100. The repetition rate of the pulses is representative of the pressure sensed by sensor 28. As the pressure increases, the repetition rate of the pulses received by diode 102 also increases.

It is preferred that microprocessor 110 is responsive to a signal from wave shaper 108 having a frequency representative of some threshold level, above which it is assumed that an inflation procedure is in process and below which it is assumed the balloon 202 is expelled of pressurizing fluid. The threshold pressure on deflation may be the same as at inflation, or it may be some lower pressure necessary to evacuate the balloon 202. In either case, the time duration between the thresholds represents the duration of the inflation. Clock 116 may be operated in response to the thresholds to determine the duration of the inflation, but it is most preferred that the time data simply be accumulated in the microprocessor or in data RAM memory 114 under the control of clock 116. At some predetermined threshold pressure, preprogrammed into microprocessor 110, the microprocessor determines that an inflation procedure is commenced. Clock 116 may also be employed to determine the total duration of multiple inflations, the duration between inflations and the duration of the entire procedure. The results are recorded in data RAM 114 and/or displayed on display 120. Likewise, current inflation pressure, maximum inflation pressure of the current inflation and maximum inflation pressure of past inflations may also be determined from the pulse repetition rate of the input signal to microprocessor 110 for display on display 120 and/or recording in data RAM 114. In addition, limits of duration, pressure and number of inflations may be preset into microprocessor (such as through keyboard 124), in which case an audible and/or visual alarm 126 may be actuated if such limits are exceeded. Display 120 may display the preset limits to keep the cardiologist appraised of conditions approaching the limits or of the number of inflations. In addition, the data may be recorded in data RAM memory 114 for future use, and/or on optional memory card 128, and/or may be printed by printer 122 for a more permanent record, such as to maintain with the patient file.

The program stored in EPROM program memory 112 controls microprocessor 110 to determine current pressure, maximum pressure, duration of inflation, number of inflations and other relevant information related to the time, pressure and duration of the procedure. Patient data, preestablished limits and other information may be inputted via keyboard 124 for use by the microprocessor and to permit printing a permanent record by printer 122 identifying the patient, time and date of procedure, attending cardiologist, and other information. Additional functions may be added to the microprocessor simply by upgrading or changing the EPROM memory chip to include desired features.

In the angioplasty procedure, it is important for the cardiologist to know the balloon diameter during inflation, since the balloon diameter is indicative of the extent of dilatation of the lesion. Most lesions can be dilated at pressures of 6 atmospheres or less, although it is not uncommon for a cardiologist to inflate a balloon to a pressure of 12 atmospheres or more to dilate a resistant lesion. Alternatively, the cardiologist may exchange the balloon for one of larger diameter to achieve the desired dilatation effect. Most dilatation balloons are stretchable to some extent over the useful pressure range of the balloon, the response of a given PTCA balloon to various pressures being known for a given temperature, such as human body temperature (37° C). Data is available for such balloons equating balloon pressure to diameter.

Advantageously, EPROM memory 112 may include a look-up table containing relational data corresponding balloon diameter to pressure (at ordinary body temperature) for a plurality of known dilatation balloons. At the start of the PTCA procedure, the cardiologist inputs data (through keyboard 124) identifying the specific dilatation balloon being used in the procedure. Microprocessor 110 responds to the identifying data to select the relational data of pressure-to-diameter for the identified balloon. As pressure data from light sensitive diode(s) 102 is processed by processor 110, the processor processes that data in comparison to the diameter data for the identified balloon in the look-up table and operates display device 120 to display the current balloon diameter. Should the cardiologist exchange catheters and employ one with a different size balloon, data identifying the new balloon is inputted through keyboard 124. The processor selects new relational data concerning the new balloon from the look-up table in EPROM 112 and causes display device 120 to display the current diameter of the new balloon. Alternatively to the lookup table, the microprocessor may contain an algorithm for calculating balloon diameter from pressure based on the identification of the dilatation balloon employed in the procedure.

The present invention thus provides a system for wireless transmission of inflation device data which permits display and recording of pertinent information during an angioplasty procedure and for permanent record thereof. The inflation device containing the transmitter is fully disposable, including the batteries contained therein. Since the apparatus employs wireless transmission, it is free of constraining cables.

Although the present invention is described in connection with wireless transmission by infrared transmission, any convenient transmission mode may be used. For example, pressure data may be transmitted from the inflation device to the receiver by ultrasonics, low frequency magnetics, or radio transmission (including very high frequency or ultra high frequency). Additionally, while the transmission is described in terms of pulse signal repetition rates, it is within the scope of the present invention to transmit modulated signals wherein pressure data is represented in a pulse, amplitude or frequency modulation of a carrier signal. The present embodiment of an infrared signal transmitted at a pulse repetition rate representative of pressure information is presently preferred because the components and design are economical and governmental approval of frequency allocation is unnecessary.

Although the present invention has been described with reference to preferred embodiments, workers skilled in the art will recognize that changes may be made in form and detail without departing from the spirit and scope of the invention.

What is claimed is:

1. An inflation device for inflating a dilatation balloon of a catheter during a percutaneous transluminal angioplasty procedure, the catheter having a lumen in fluid communication with the dilatation balloon, the inflation device comprising:

a housing having a chamber for containing a fluid and a plunger within the chamber for changing fluid pressure in the chamber, the housing comprising first and second members, fastening means on the first and second members for removably fastening the first and second members together to form an enclosure;

means for connecting the catheter to the housing so that the lumen of the catheter is in fluid communication with the chamber;

sensing means responsive to fluid pressure within the chamber for deriving a signal representative of fluid pressure within the chamber; and a wireless transmitter connected to the sensing means for wireless transmission of a broadcast signal containing data representative of the signal derived by the sensing means, the wireless transmitter and sensing means comprising an electronic circuit having first and second circuit portions within the enclosure and electrical connection means connecting the first and second circuit portions together, one of the circuit portions being mechanically supported by one of the first and second members, a battery support within the enclosure for operating the electronic circuit, the fastening means permitting separation of the first and second members to permit removal of the battery, wherein the electronic circuit includes a pressure transducer mechanically supported by the first member and operatively connected to the chamber to provide an electronic signal representative of fluid pressure within the chamber, the first circuit portion being mechanically supported by the second member, said electrical connection means including a unitary frangible portion electrically connecting the transducer to the first circuit portion and so disposed and arranged as to break said frangible portion upon separation of the first and second members, and thereby electrically disconnect the transducer from the first circuit portion prohibiting use of the electrical connection means.

2. An inflation device according to claim 1 further including a strip of insulator material removably insulating the battery from the electronic circuit, the housing having an opening through which a portion of the strip extends, the strip being removable to electrically connect the battery to the electronic circuit.

3. An inflation device according to claim 1 wherein the sensing means is responsive to fluid pressure within the chamber to provide a pulse signal having a pulse repetition rate representative of fluid pressure within the chamber and the transmitter includes infrared transmission means for transmitting infrared pulses at a repetition rate representative of the pulse signal.

4. An inflation device according to claim 3 wherein the infrared transmission means comprises a plurality of infrared transmitters mounted to the exterior of the housing in spaced relation.

5. An inflation device according to claim 1 further including a switch mounted to the housing for initiating operation of the electronic circuit.

6. An inflation device according to claim 5 wherein the electronic circuit includes a latch responsive to the operation of the switch to latch the electronic circuit to an operating condition.

7. An inflation device for inflating a dilatation balloon of a catheter during a percutaneous transluminal angioplasty procedure, the catheter having a lumen in fluid communication with the dilatation balloon, the inflation device comprising:

first and second members;

fastening means carried on the first and second members for removably fastening the first and second members together to form an enclosure;

a chamber carried by the first member for containing a fluid;

a plunger within the chamber, the plunger being operable to change fluid pressure in the chamber;

means for connecting the catheter to the chamber so that the lumen of the catheter is in fluid communication with the chamber;

an electronic circuit in the enclosure including sensing means responsive to fluid pressure within the chamber, the electronic circuit comprising first and second circuit portions and electrical connection means connecting the first and second circuit portions together, one of the circuit portions being mechanically supported by one of the first and second members, the electronic circuit including a pressure transducer mechanically supported by the first member and operatively connected to the chamber to provide an electronic signal representative of fluid pressure within the chamber, the first circuit portion being mechanically supported by the second member, the electrical connection means including a first unitary frangible portion electrically connecting the transducer to the first circuit portion and so disposed and arranged as to break the frangible portion upon separation of the first and second members and thereby electrically disconnect the transducer from the first circuit portion prohibiting the use of the electrical connection means;

a battery supported within the enclosure for operating the electronic circuit; and the fastening means permitting separation of the first and second members to permit removal of the battery.

8. An inflation device according to claim 7 wherein the connection means includes a second frangible portion so disposed and arranged as to break electrical connection between the first and second circuit portions upon separation of the first and second members.

9. An inflation device according to claim 7 wherein the first and second members together form a generally cylindrical housing, the fastening means comprising a first fastener supported by the first member and a second fastener supported by the second member, the first and second fasteners being engagable to fasten the first and second members together to form the housing and being disengagable upon relative rotation of the first and second members to permit separation of the first and second members.

10. An inflation device according to claim 9 wherein one of the first and second fasteners includes a circumferentially-disposed ramp surface and a circumferentially-disposed recess forming a radial lip, and the other of the first and second fasteners includes a circumferentially-disposed clamp surface, the first and second fasteners being engaged by relatively rotating the first and second members so that the clamp surface rotationally engages the ramp surface to cam over the radial lip and be received in the recess.

11. An inflation device for inflating a dilatation balloon of a catheter during a percutaneous transluminal angioplasty procedure, the catheter having a lumen in fluid communication with the dilatation balloon, the inflation device comprising:

a housing having an opening, the opening extending outside the housing;

a chamber carried by the housing for containing a fluid;

a plunger within the chamber, the plunger being operable to change fluid pressure in the chamber;

means for connecting the catheter to the chamber so that the lumen of the catheter is in fluid communication with the chamber;

an electronic circuit including sensing means responsive to fluid pressure within the chamber, the electronic circuit being located within the housing;

a battery supported within the housing for operating the electronic circuit;

a strip of insulator material extending through the opening and removably insulating the battery from the electronic circuit, the strip being removable to electrically connect the battery to the electronic circuit.

12. An inflation device according to claim 11 further including a switch mounted to the housing for initiating operation of the electronic circuit.

13. An inflation device according to claim 12 wherein the electronic circuit includes a latch responsive to the operation of the switch to latch the electronic circuit to an operation condition.

14. An inflation device according to claim 11 wherein the electronic circuit includes a pressure transducer operatively connected to the chamber to provide an electronic signal representative of the fluid pressure within the chamber, and a wireless transmitter connected to the electronic circuit for wireless transmission of data representative of the electronic signal derived by the pressure transducer.

15. An inflation device according to claim 14 wherein the electronic circuit includes an oscillator responsive to the electronic signal from the pressure transducer to provide a signal having a frequency representative of fluid pressure within the chamber.

16. An inflation device according to claim 15 wherein the electronic circuit further includes a multivibrator responsive to the oscillator to provide a pulse signal having a repetition rate representative of the frequency of the signal provided by the oscillator and having a small pulse duration.

17. An inflation device according to claim 16 wherein the pulse repetition rate varies between about 5 and 15 KHz and the pulse duration is of the order of between about 2 and 5 microseconds.

18. An inflation device according to claim 14 wherein the electronic circuit is responsive to the pressure transducer to provide a pulse signal having a pulse repetition rate representative of fluid pressure within the chamber, and the transmitter includes infrared transmission means for transmitting infrared pulses at a repetition rate representative of the pulse signal.

19. An inflation device according to claim 18 wherein the infrared transmission means comprises a plurality of infrared transmitters mounted to the exterior of the housing in spaced relation.

20. An inflation device according to claim 18 wherein the pulse repetition rate varies between about 5 and 15 KHz and the pulse signal has a pulse duration of the order of between about 2 and 5 microseconds.

21. A monitoring system for inflating and monitoring the condition of a dilatation balloon of a catheter during a percutaneous transluminal angioplasty procedure, the catheter having a lumen in fluid communication with the dilatation balloon, the monitoring system comprising:

an inflation device comprising a housing supporting a chamber for containing a fluid, a plunger within the chamber for changing the pressure of fluid in the chamber, means for connecting the catheter to the chamber so that the lumen of the catheter is in fluid communication with the chamber, pressure sensing means within the housing and responsive to fluid pressure within the chamber for providing a signal representative of the fluid pressure within the chamber, and a wireless transmitter supported by the housing and connected to the circuit and responsive to the signal provided by the pressure sensing means for wireless transmission of a broadcast signal containing data representative of the fluid pressure within the chamber, the housing of the inflation device comprising first and second members, fastening means on the first and second members for removably fastening the first and second members together to form an enclosure, the wireless transmitter and sensing means comprising an electronic circuit having first and second circuit portions within the enclosure and electrical connection means connecting the first and second circuit portions together, one of the circuit portions being mechanically supported by one of the first and second members, a battery supported within the enclosure for operating the electronic circuit, the fastening means permitting separation of the first and second members to permit removal of the battery, the electronic circuit including a pressure transducer mechanically supported by the first member and operatively connected to the chamber to provide an electronic signal representative of fluid pressure within the chamber, the first circuit portion being mechanically supported by the second member, the electrical connection means including a unitary frangible portion electrically connecting the transducer to the first circuit portion and so dispose and arranged as to break the frangible portion upon separation of the first and second members and thereby electrically disconnect the transducer from the first circuit portion prohibiting use of the electrical connection means; and a remote receiver comprising a broadcast signal sensor responsive to the broadcast signal for deriving a data signal, a clock providing a clock signal, a processor connected to the broadcast signal sensor and clock for processing the data signal and the clock signal to derive information concerning pressure within the chamber and duration of inflation, and a display device connected to the processor for displaying the information derived by the processor.

22. A monitor system according to claim 21 further including a strip of insulator material removably insulating the battery from the electronic circuit, the housing having an opening through which a portion of the strip extends, the strip being removable to electrically connect the battery to the electronic circuit.

23. A monitor system according to claim 21 further including a switch mounted to the housing for initiating operation of the electronic circuit.

24. A monitor system according to claim 23 wherein the electronic circuit includes a latch responsive to the operation of the switch to latch the electronic circuit to an operating condition.

25. A monitor system according to claim 21 wherein the remote receiver includes a memory having a look-up table containing relational data relating the diameter of a dilatation balloon to pressure within the respective balloon for a plurality of dilatation balloons, the processor having input means for receiving data identifying the dilatation balloon in fluid communication with the catheter connected to the chamber, the processor being responsive to the dilatation balloon identification data and the data signal derived by the broadcast signal sensor to select diameter information from the look-up table, the display device being responsive to the processor to display diameter information.

26. A monitor system according to claim 21 wherein the sensing means of the inflation device includes a pressure transducer in fluid communication with the chamber producing a signal having a magnitude representative of fluid pressure within the chamber, and an oscillator responsive to the magnitude of the signal from the pressure transducer to provide a signal having a frequency representative of fluid pressure within the chamber.

27. A monitor system according to claim 26 wherein the sensing means further includes a multivibrator responsive to the oscillator to provide a pulse signal having a repetition rate representative of the frequency of the signal provided by the oscillator and having a small pulse duration.

28. A monitor system according to claim 27 wherein the pulse repetition rate varies between about 5 and 15 KHz and the pulse duration is of the order of between about 2 and 5 microseconds.

29. A monitor system according to claim 27 wherein the wireless transmitter includes infrared transmission means responsive to the oscillator to transmit infrared pulses at a repetition rate representative of the pulse signal.

30. A monitor system according to claim 29 wherein the infrared transmission means comprises a plurality of infrared transmitters mounted to the exterior of the housing in spaced relation.

31. A monitor system according to claim 29 wherein the broadcast signal sensor of the remote receiver includes an infrared detector responsive to infrared pulses transmitted by the wireless transmitter to produce the data signals.

* * * * *

UNITED STATES PATENT AND TRADEMARK OFFICE
CERTIFICATE OF CORRECTION

PATENT NO. : 5,318,533
DATED : June 7, 1994
INVENTOR(S) : DANIEL O. ADAMS, DAVID J. HASKVITZ, THOMAS J. HOLMAN, WILLIAM H. PENNY, DAVID J. SERDAR, JOHN M. YATES It is certified that error appears in the above-indentified patent and that said Letters Patent is hereby corrected as shown below:

Col. 5, line 2, delete "are,", insert --are--

Col. 7, line 44, delete "transmitter", insert --transmitter 80--

Signed and Sealed this

Eleventh Day of October, 1994

Attest:

BRUCE LEHMAN

*Attesting Officer*  *Commissioner of Patents and Trademarks*